(12) United States Patent
Rindy et al.

(10) Patent No.: US 7,886,783 B2
(45) Date of Patent: Feb. 15, 2011

(54) ANESTHETIC VAPORIZER FILLING SYSTEM

(75) Inventors: Ryan W. Rindy, McFarland, WI (US); Robert Q. Tham, Middleton, WI (US)

(73) Assignee: The General Electric Company, Schenectady, NY (US)

( * ) Notice: Subject to any disclaimer, the term of this patent is extended or adjusted under 35 U.S.C. 154(b) by 154 days.

(21) Appl. No.: 12/471,151

(22) Filed: May 22, 2009

(65) Prior Publication Data

US 2010/0294276 A1    Nov. 25, 2010

(51) Int. Cl.
*B65B 1/04*    (2006.01)
(52) U.S. Cl. .................. 141/351; 141/302; 141/346; 141/363; 141/364; 141/366
(58) Field of Classification Search ............ 141/2, 141/18, 98, 346–351, 363–366
See application file for complete search history.

(56) References Cited

U.S. PATENT DOCUMENTS

| | | | |
|---|---|---|---|
| 5,381,836 A | 1/1995 | Braatz et al. | |
| 5,505,236 A * | 4/1996 | Grabenkort et al. | 141/329 |
| 5,617,906 A | 4/1997 | Braatz et al. | |
| 5,676,186 A * | 10/1997 | Vanderploeg | 141/347 |
| 5,687,777 A | 11/1997 | Dobson et al. | |
| 5,799,711 A * | 9/1998 | Heinonen et al. | 141/18 |
| 6,817,390 B2 * | 11/2004 | Falligant et al. | 141/352 |
| 6,929,041 B2 | 8/2005 | Falligant et al. | |

FOREIGN PATENT DOCUMENTS

EP    0909567 A2    4/1999

OTHER PUBLICATIONS

Search Report & Written Opinion for PCT/US2010/028477, Aug. 6, 2010.

* cited by examiner

*Primary Examiner*—Timothy L Maust
(74) *Attorney, Agent, or Firm*—Andrus, Sceales, Starke & Sawall, LLP

(57) ABSTRACT

A system for the delivery of a liquid anesthetic agent to a sump of an anesthetic vaporizer includes a filler assembly rotatable about a pivot point. The filler assembly further includes a sump valve that controls fluid communication between the filler assembly and the sump. An adapter is coupled with the filler spout and includes a sealing surface that forms a seal against fluid communication between the anesthetic bottle and the adapter. The filler assembly, the filler spout, and the adapter are rotated about the pivot point along the rail. The rotation of the filler assembly, the filler spout, and the adapter about the pivot point opens the sump valve and the seal between the adapter and the anesthetic bottle.

20 Claims, 10 Drawing Sheets

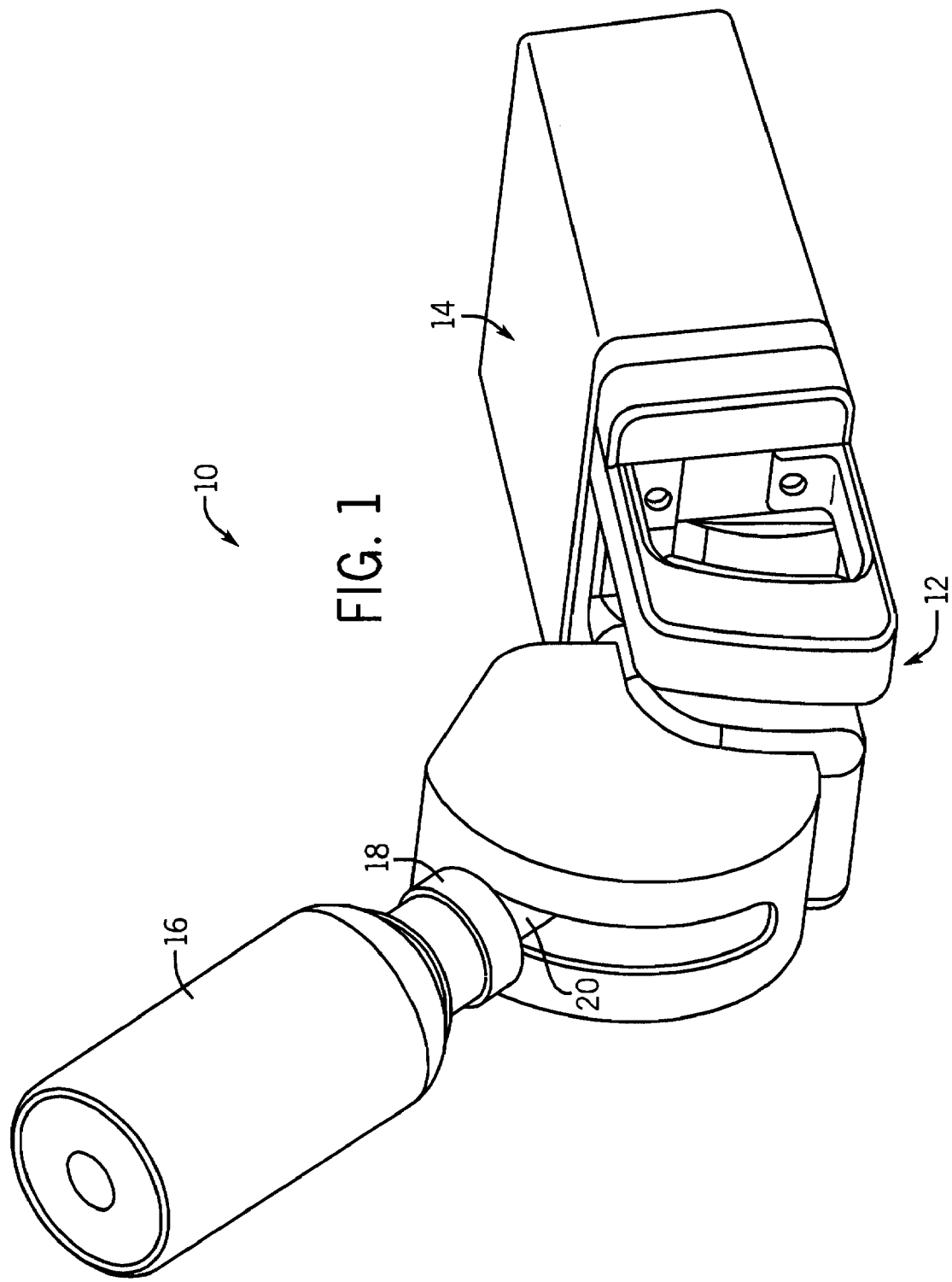

ANESTHETIC VAPORIZER FILLING SYSTEM

BACKGROUND

The present disclosure generally relates to a system for transferring a liquid anesthetic agent from an anesthetic bottle to an anesthetic vaporizer. More specifically, the present disclosure relates to an anesthetic vaporizer, an adapter for an anesthetic bottle, and anesthetic vaporizer filling system.

Anesthetic agents are typically volatile substances with relatively low boiling points and high vapor pressures. Anesthetic agents can be flammable and explosive in both the liquid and vapor states. Further, inhalation of vapor by healthcare personnel in an area near where the anesthetic agent is being used can cause drowsiness, reduced attentiveness, and/or reduced reaction time. An anesthetic agent is administered to a patient during anesthesia through the use of an anesthetic vaporizer. The anesthetic agent is supplied to the patient as a vapor from a reservoir of anesthetic liquid stored in an internal sump within a vaporizer. The anesthetic agent is typically mixed with oxygen and/or nitrous oxide prior to its delivery to the patient for improved inhalation and/or absorption of the anesthetic agent by the patient's body.

Therefore, it is desirable to maintain the anesthetic agent in the sump sealed against the leakage of any of the anesthetic liquid, or vapor, except for desired release controlled by the vaporizer. Leakage of anesthetic liquids or vapors from the sump may result in exposing the personnel around the vaporizer to the risks indicated above, but may also contribute to waste or loss of the anesthetic agent itself, or the introduction of contaminants to the anesthetic agent stored in the sump.

Presently, many types of anesthetic agents are available for use during anesthesia and delivered by a vaporizer. These anesthetic agents include, but are not limited to: Enflurane (2-chloro-1,1,2-trifluoromethyl), Halothane (1-bromo-1-chloro-2,2,2,-trifluoroethane), Isoflurane (1-chloro-2,2,2-trifluoroethyl difluoromethyl ether), Sevoflurane (fluoromethyl 2,2,2-trifluoror-1-(trifluoromethyl)ethyl ether), and Desflurane (2-(difluoromethoxy)-1,1,1,2-tetrafluoroethane).

Each of these anesthetic agents have different properties and vaporizers are designed to deliver each anesthetic agent differently depending upon the properties of the specific anesthetic agent. Therefore, it is important that the correct type of anesthetic agent is delivered to the vaporizer sump. Various conventions and/or standards, such as those defined by the International Standardization Organization (ISO) help to ensure that the correct anesthetic agent is delivered into a proper sump of the vaporizer. These conventions and standards include the use of various colors to indicate components directed towards the use of specific anesthetic agents. Additionally, the anesthetic bottle and the connection for the anesthetic bottle to the vaporizer are indexed such as through projections, keys, and/or bottle dimensions to ensure that only the proper anesthetic bottle fits the designated vaporizer components designed for that type of anesthetic. This greatly reduces the probability of inadvertently using the wrong type of anesthetic agent within the vaporizer.

BRIEF DISCLOSURE

A system for delivery of a liquid anesthetic agent to a sump of an anesthetic vaporizer is disclosed herein. Embodiments of the system include a filler assembly rotatable above a pivot point, the filler assembly comprising a sump valve controlling a fluid connection between the sump and the filler assembly. A filler spout is connected in fluid communication with the filler assembly. An adapter is coaxial to a bottle cap which is suitable for connection to an anesthetic bottle containing a liquid anesthetic agent, the adapter has a sealing surface that engages the bottle cap to form a seal against fluid communication between the anesthetic bottle and the adapter. The adapter couples with the filler spout to form a fluid seal between the filler spout and the adapter. A rail is affixed to the anesthetic vaporizer, the rail has a cam surface. A rib of the adapter contacts the rail and the bottle cap contacts the rail. Rotation of the bottle cap and the adapter about the pivot point causes the cam surface of the rail to disengage the sealing surface of the adapter from the bottle cap and open the adapter to fluid communication with the anesthetic bottle.

An adapter apparatus for connection between an anesthetic bottle and an anesthetic vaporizer is further disclosed herein. An embodiment of the adapter includes a bottle cap configured at one end for connection to an anesthetic bottle. The bottle cap includes an open interior. An adapter includes a bottle end and vaporizer end, the bottle end terminates in a sealing surface that couples with the bottle cap to form a fluid seal. The vaporizer end of the adapter is configured to couple with the anesthetic vaporizer and further includes a rib that extends radially outward from the adapter. An expansive force applied between the bottle cap and the rib of the adapter increases the distance between the bottle cap and the rib of the adapter and separates the sealing surface of the adapter from the bottle cap, thereby opening fluid communication between the bottle cap and the adapter.

An anesthetic vaporizer is further disclosed herein. An embodiment of the anesthetic vaporizer includes a sump that to receives and stores liquid anesthetic agent. A filler assembly is connected to the sump through a sump valve. The sump valve is actuated by the rotation of the filler assembly about a pivot point of the filler assembly. A filler spout is connected to the filler assembly and extends radially away from the pivot point of the filler assembly. The filler spout has a hollow interior for fluid communication therethrough and is configured to establish fluid communication with an anesthetic bottle. A filler valve positioned between the filler assembly and the filler spout is movable between a sealing position wherein the filler valve blocks fluid communication between the filler spout and the filler assembly and an open position wherein the fluid passes the filler valve between the filler spout and the filler assembly. The anesthetic vaporizer further includes a rail having a cam surface at a varying distance from the pivot point of the filler assembly.

BRIEF DESCRIPTION OF THE DRAWINGS

In the drawings:

FIG. 1 is a perspective view of a system for the delivery of a liquid anesthetic agent;

DETAILED DISCLOSURE

Figure 2A:
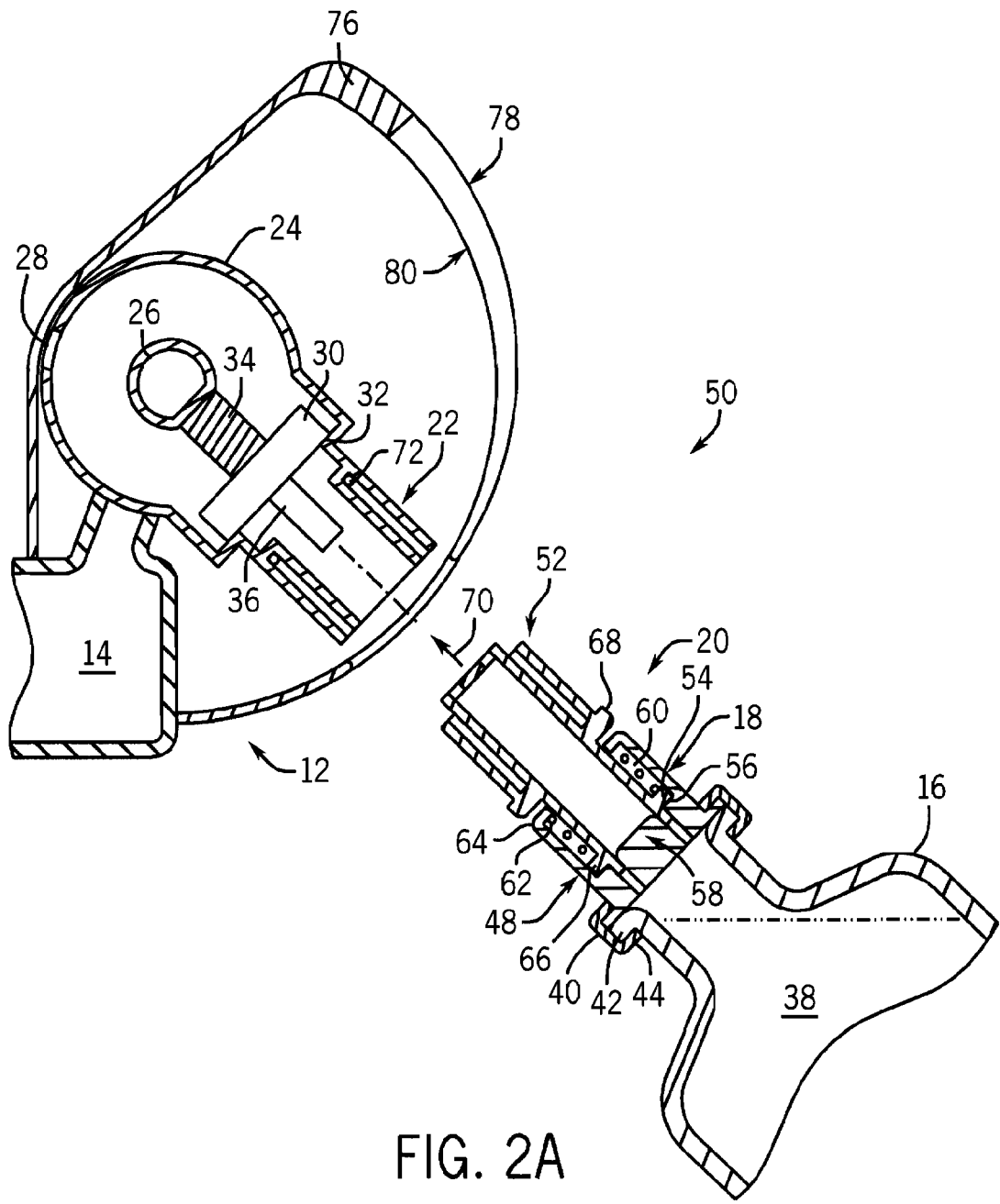
FIGS. 2A-C depicts an embodiment of a system for the delivery of a liquid anesthetic agent.

FIG. 1 is a perspective view illustrating a system 10 for the delivery of a liquid anesthetic agent to a sump of an anesthetic vaporizer. The system 10 includes a vaporizer filling system 12 that connects with the rest of a vaporizer (not depicted).

The vaporizer filling system 12 includes a sump 14 (internal) within which the liquid anesthetic agent is stored.

The system 10 further includes an anesthetic bottle 16 that holds a liquid anesthetic agent for delivery into the sump 14 of the vaporizer filling system 12. A bottle cap 18 is attached to the anesthetic bottle 16. The bottle cap 18 may be connected to the anesthetic bottle 16 by a variety of known implementations for attaching a cap, such as, but not limited to, screw fitting to mate with a thread inside the bottle, pressure fitting, or by a crimped flange of the bottle cap 18 mating with the lip of the anesthetic bottle 16.

The bottle cap 18 is further connected to an adapter 20 that facilitates the connection between the anesthetic bottle 16 and the vaporizer filling system 12. The adapter 20 engages a filler spout (not depicted) of the vaporizer filling system 12 such as to connect the anesthetic bottle 16 in fluid communication with the vaporizer filling system 12.

In practice, prior to the use of the vaporizer to delivery anesthesia to the patient, a clinician obtains an amount of a specific anesthetic agent as stored in the anesthetic bottle 16. The clinician uses the adapter 20 coupled with the anesthetic bottle 16 to create a fluid tight seal between the bottle 16 and the filler spout 22. Once a fluid tight seal has been established between the anesthetic bottle 16 and the vaporizing filling system 12, the liquid anesthetic agent may be delivered from the anesthetic bottle 16 to the sump 14 of the vaporizer filing system 12.

Figure 2B:
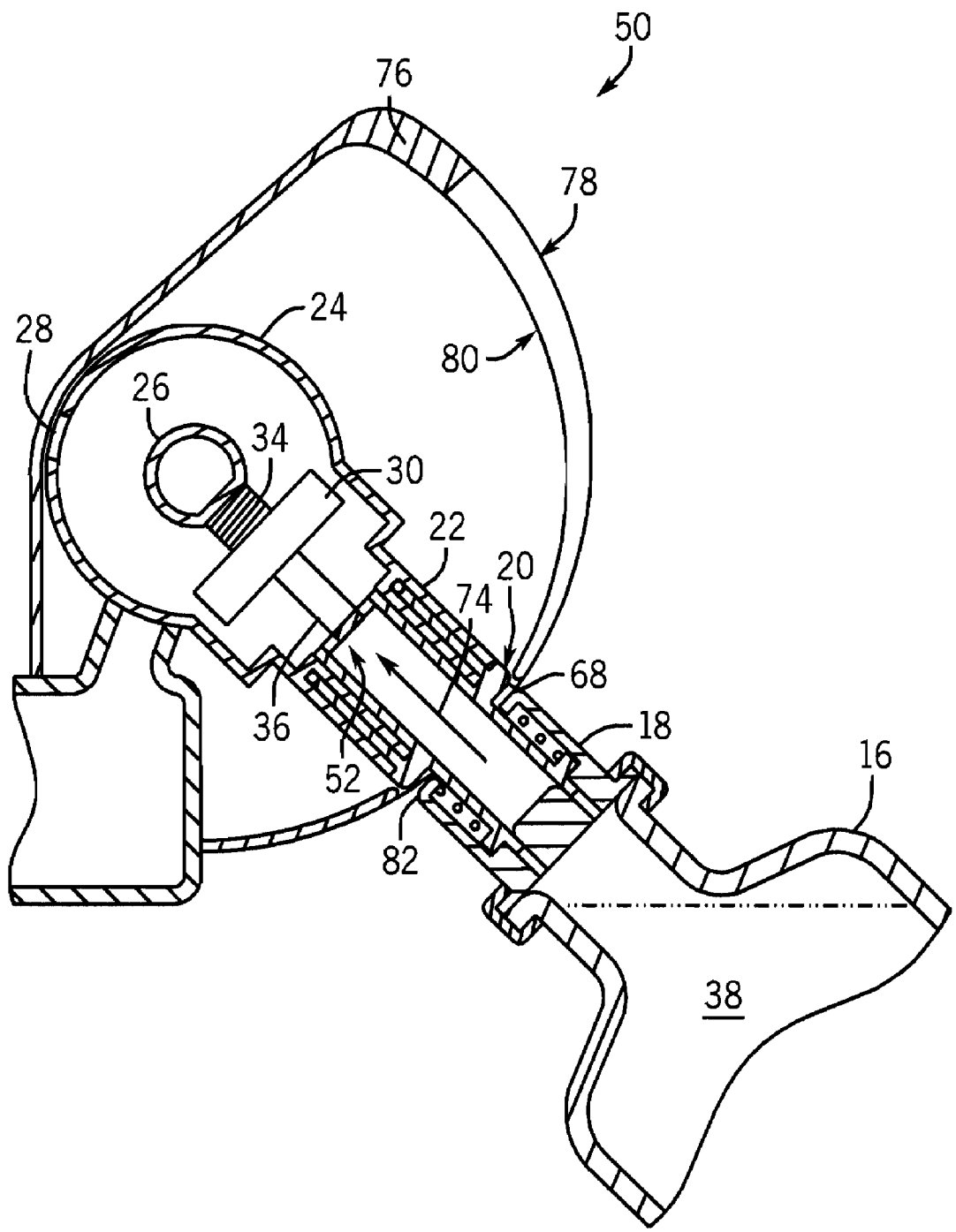
Figure 2C:
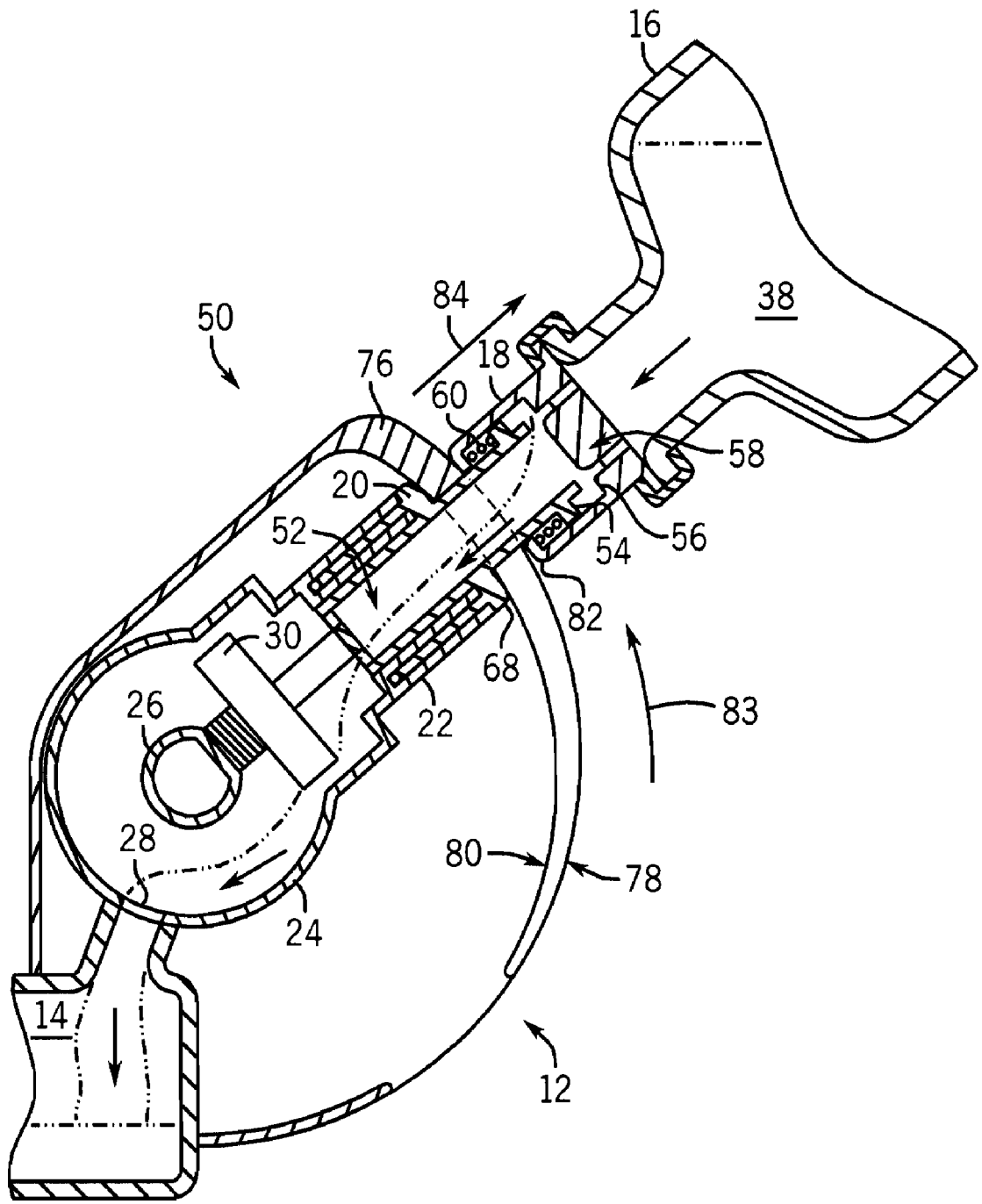

FIGS. 2A-C depict an embodiment 50 of the system for delivery of a liquid anesthetic agent to an anesthetic vaporizer. It should be noted that in the figures like numerals are used to reference similar components common among the embodiments disclosed herein.

Referring to FIG. 2A, the system 50 includes the vaporizer filling system 12 of the vaporizer (not depicted). The vaporizer filling system 12 includes a sump 14 and a filler spout 22. The filler spout 22 is connected to the sump 14 through a filler assembly 24. The filler assembly 24 includes a pivot point 26, about which the filler assembly 24 is able to rotate.

The filler assembly 24 further includes a sump valve 28. The sump valve 28 controls the fluid communication between the sump 14 and the filler assembly 24. In an embodiment, the filler valve 28 operates as a ball valve such that rotation of the filler assembly 24 about the pivot point 26 moves the filler valve 28 from a sealing position wherein fluid communication between the filler assembly 24 and the sump 14 is prevented and an open position in which fluid communication between the filler assembly 24 and the sump 14 is allowed.

The filler assembly 24 is separated from the filler spout 22 by a filler valve 30. The filler valve 30, similar to the sump valve 28, operates between a sealing position wherein fluid communication between the filler spout 22 and the filler assembly 24 is prevented and an open position wherein fluid communication between the filler spout 22 and the filler assembly 24 is allowed.

The filler valve 30 forms a seal 32 between the filler assembly 24 and the filler spout 22. In an embodiment, the seal 32 is created by mating sealing surfaces on the filler assembly 24 and the filler spout 22. These surfaces may be treated with a material, such as an elastomeric material, that promotes the creation of the seal 32 when the filler valve 30 engages the filler spout 22.

The filler valve 30 further includes a spring 34 that extends between the filler valve 30 and the filler assembly 24. In an embodiment, the spring 34 extends between the filler valve 30 and the pivot point 26. The spring 34 exerts a biasing force on the filler valve 30 such as to bias the filler valve 30 into the sealing position, preventing fluid communication between the filler spout 22 and the filler assembly 24. It should be noted that in alternative embodiments, the spring 34 may be replaced by alternative devices suitable for performing the biasing function of the spring 34 as disclosed herein. The filler valve 30 further includes a projection 36 that extends into the filler spout 22 in a direction away from the filler assembly 24.

The system 50 further includes the anesthetic bottle 16 that holds liquid anesthetic agent 38. The bottle 16, containing the liquid anesthetic agent 38, is capped by a bottle cap 18. The bottle cap 18, as depicted, is attached to the bottle 16 by a flange 40 that extends from the cap 18 around a lip 42 of the bottle 16 and terminates in a crimped end 44, securing the bottle cap 18 to the anesthetic bottle 16. Alternatively, it should be noted that the bottle cap 18 may be attached to the anesthetic bottle 16 in a variety of other ways, including, but not limited to, pressure fitting and a threaded engagement between threads on the bottle cap 18 and the bottle 16.

An adapter 20 is disposed within a hollow interior of the bottle cap 18 and is coaxial to the bottle cap 18. The adapter 20 terminates in a bottle end 48 within the bottle cap 18. The other end of the adapter 20 extends outside of the bottle cap 18 and extends away from the bottle cap 18, terminating in a vaporizer end 52.

The bottle end 48 of the adapter 20 includes a sealing surface 54. The sealing surface 54 engages the bottle cap 18 at a sealing seat 56. The sealing seat 56 may be an annular seat extending around the interior of the bottle cap 18. The sealing surface 54 of the adapter 20 may similarly be annular in shape such as to mate with the sealing seat 56 in order to form a seal against fluid communication between the anesthetic bottle 16 and the adapter 20.

A bottle valve 58 formed of the sealing surface 54 of the bottle end 48 of the adapter 20 and the sealing seat 56 of the bottle cap 18 operates between a sealing position wherein fluid communication between the anesthetic bottle 16 and the adapter 20 is prevented in an open position wherein fluid communication between the anesthetic bottle 16 and the adapter 20 is allowed. The bottle valve 58 further includes a spring 60 within the bottle cap 18 that extends between an end inner surface 62 of a shoulder 64 of the bottle cap 18 and a flange 66 on the bottle end 48 of the adapter 20. The spring 60 applies a biasing force against the flange 66 such as to bias the adapter 20 and the bottle cap 18 to hold the bottle valve 58 in the sealing position, whereby fluid communication between the anesthetic bottle 16 and the adapter 20 is prevented. The bottle valve 58 is moved to the open position by a force in the direction away from the anesthetic bottle 16 that overcomes the biasing force of the spring 60 in the opposite direction.

In alternative embodiments, the bottle valve 58 may be formed of the sealing surface 54 of the adapter and the bottle cap 18 in a variety of valve configurations. These alternative configurations of the bottle valve 58 may be different from the disclosed sealing surface 54 and the sealing seat 56. These alternative configurations may include a ball valve or a spool valve, but is not to be limited solely to these disclosed variations.

The adapter 20 further includes a rib 68 that extends radially outward from the adapter 20 on a portion of the adapter 20 that extends beyond the bottle cap 18.

The adapter 20 is moved in the direction of arrow 70 so that the adapter 20 coaxially engages the filler spout 22. The adapter 20 may engage the filler spout 22 in a variety of known ways of engagement. This may include, but is not limited to, pressure fitting and keyed engagements. The filler spout 22 includes an annular ring 72 such as to create a sealing surface on the filler spout 22. Alternatively, a radially inward surface of the filler spout 22 may be treated with a material, such as an elastomeric material that engages with the adapter 20 to form a seal. Additionally, the adapter 20 may include a sealing surface, such as with an elastomeric material on a radially outward surface of the adapter 20. Therefore, when the adapter 20 and the filler spout 22 engage, a seal is created against fluid communication outside of the adapter 20 and the filler spout 22. In an alternative embodiment, the adapter 20 may be sized in order to fit radially outward of the filler spout 22, such that a radially inward surface of the adapter 20 engages a radially outward surface of the filler spout 22. While it is herein described that the adapter 20 engages the filler spout 22, it is to be understood that the adapter 20 may alternatively be coupled with the filler spout 22 which includes both direct and indirect connections between the adapter 20 and the filler spout 22.

FIG. 2B shows the system 50 after the adapter 20 has been fully inserted into the filler spout 22. The adapter 20 therefore engages the filler spout 22 such as to establish fluid communication between the adapter 20 and the filler spout 22, while forming a fluid impervious seal between the adapter 20, the filler spout 22, and the ambient atmosphere.

As the adapter 20 is inserted into the filler spout 22, the vaporizer end 52 of the adapter 20 engages the projection 36 extending from the filler valve 30 into the filler spout 22. As the adapter 20 is inserted further into the filler adapter 22, the vaporizer end 52 of the adapter 20 pushes on the projection 36 in the direction of arrow 74 which is towards the pivot point 26 of the filler assembly 24. The force in the direction of arrow 74 overcomes the biasing force created by the spring 34 such that the filler valve 30 is moved from the sealing position, into an open position thereby opening fluid communication between the adapter 20, filler spout 22, and the filler assembly 24.

As noted previously, it is desirable for the liquid anesthetic agent 38 to be transferred to the sump 14 of the vaporizer without any of the anesthetic agent leaking to the ambient atmosphere in liquid or gas form. Therefore, as seen in FIG. 2B, the two reservoirs of anesthetic agent, namely the anesthetic bottle 16 and the sump 14, are sealed by the respective sump valve 28 and the bottle valve 58 while the internal filler valve 30 is opened, prior to communication of the liquid anesthetic agent 38 to the sump 14.

FIG. 2C further depicts the operation of the system 50. The vaporizer filling system 12 further includes a rail 76 with an outer cam surface 78. The outer cam surface 78 diverges radially outward from the pivot point 26. From the position depicted in FIG. 2B, the filler assembly 24, filler spout 22, adapter 20, and anesthetic bottle 16 are rotated about the pivot point 26 of the filler assembly 24. As these components are rotated about the pivot point 26, a top surface 82 of the bottle cap 18 engages the cam surface 78 of the rail 76. The rib 68 on the adapter 20 contacts an inner surface 80 of the rail 76.

As the filler assembly 24, filler spout 22, adapter 20, and anesthetic bottle 16 are further rotated about the pivot point 26 along the rail 76, the rail 76 and the cam surface 78 apply an expansive force in the direction of arrow 84 against the top surface 82 of the bottle cap 18. The rib 68, contacting the inner surface 80 of the rail 78, maintains the adapter 20 at a fixed radial distance from the pivot point 26. The force in the direction of arrow 84 forces the bottle valve 58 to move from a sealing position, to an open position, thereby opening the bottle valve 58 to fluid communication between the anesthetic bottle 16 and the adapter 20. More specifically, the force in the direction of arrow 84 overcomes the bias force of the spring 60 and separates the sealing surface 54 of the adapter 20 from the sealing seat 56 of the bottle cap 18.

In an alternative embodiment, the rib 68 of the adapter 20 does not contact the inner surface 80 of the rail 76. Rather, the adapter 20 may be maintained in a fixed radial distance from the pivot point 26, or captured, in an alternative fashion. One such alternative may include the engagement or coupling between the adapter 20 and the filler spout 22. However, this is not intended to be limiting on the scope of the ways in which the adapter 20 may be captured.

In a further alternative embodiment, the rail 76 includes a cam surface on the inner surface 80 of the rail 76. The cam surface on the inner surface 80 diverges radially inward towards the pivot point 26. The outer surface 78 of the rail 76 does not include a cam surface and contacts the bottle cap 18 and maintains the bottle cap 18 at the same radial distance from the pivot point 26 as the bottle cap 18 is moved along the rail 76 in the direction of arrow 83. The cam of the inner surface 80 applies the expansive force against the rib 68 of the adapter 20. This forces the vaporizer end 52 of the adapter 20 further into the filler spout 22. This displacement overcomes the biasing force placed on the bottle end 48 of the adapter by the spring 60 and separates the sealing surface 54 of the adapter from the sealing seat 56 of the bottle cap 18. This opens the adapter to fluid communication from the bottle 16.

In an additional feature of an alternative embodiment, upon insertion of the adapter 20 into the filler spout 22, the adapter 20 does not engage the filler valve 30, or the projection 36 of the filler valve 30. Alternatively, the adapter 20 may engage the filler valve 30, but does not apply a force sufficient to move the filler valve 30 from the closed position into the open position. This may be due to an insufficient force applied by the adapter 20 to the filler valve 30 overcome the biasing force applied by the spring 34 against the filler valve 30.

In this embodiment, the cam action of the cam on the inner surface 80 against the rib 68 of the adapter 20 not only applies an expansive force between the rib 68 of the adapter 20 and the bottle cap 18 such as to separate the sealing surface 54 from the sealing seat 56 in order to open the bottle valve 58. The cam action of the inner surface 80 also forces the adapter 20 further into the filler spout 22 in the direction of the pivot point 26. This causes the adapter 20 to engage the filler valve 30, if the adapter 20 has not already engaged the filler valve 30. The adapter 20 moves the filler valve 30 from the sealing position into the open position such as to open fluid communication between the adapter 20 and the filler spout 22 with the filler assembly 24.

Additionally, as the filler assembly 24 rotates about the pivot point 26, the sump valve 28 is rotated into a position aligned with the sump 14, such that the sump valve 28 is opened from a sealing position into an open position and fluid communication between the filler assembly 24 and the sump 14 is permitted.

Therefore, once the adapter 20 is fully inserted into the filler spout 22, and the filler assembly 24, filler spout 22, adapter 20, and anesthetic bottle 16 are rotated into position, the bottle valve 58, filler valve 30, and sump valve 28 are all opened to fluid communication. Liquid anesthetic agent 38 is therefore allowed to flow from the anesthetic bottle 16 into the sump 14 of the vaporizer filling system 12.

In an alternative control of the bottle valve 58, filler valve 30, and sump valve 28, the mechanisms for opening and closing these valves as disclosed herein are coordinated with specific positions of the rotation of the filler assembly 24, filler spout 22, adapter 20, and bottle 16 along the rail 76 about the pivot point 26. This coordination may be achieved by the positioning of the valves (28, 30, 58) themselves or the components that actuate these valves, or the biasing of these valves in the closed position, such as by spring 34 and spring 60.

In an embodiment, the sump valve 28, filler valve 30, and bottle valve 58 may be coordinated to open in that order as the filler assembly 24, filler spout 22, adapter 20, and bottle 16 are rotated along the rail 76 in the direction of arrow 83. In this embodiment, the sump valve 28 opens first as the filler assembly 24 is rotated about the pivot point 26. Then, the filler valve 30 is opened as the filler assembly 24, the filler spout 22, and the adapter 20 are rotated further about the pivot point 26. Finally, the bottle valve 58 is opened as the adapter 20, the bottle cap 18, and the anesthetic bottle 16 are rotated about the pivot point 26 into the final vaporizer filling position.

An advantage of this coordination of the opening of the sump valve 28, the filler valve 30, and the bottle valve 58 allows for maximum guard against leakage of the anesthetic agent 38, whether the anesthetic agent 38 is located in the sump 14 or the anesthetic bottle 16. Hence, it is desirable to open the bottle valve 58 last when the sump valve 28 and the fill valve 30 have already been opened such that the anesthetic agent 38 has a clear path to fluid communication with the sump valve 14. Similarly, it is desirable to close the bottle valve 58 first, such that any remaining anesthetic agent 38 in the anesthetic bottle 16 is sealed into the bottle 16. This also allows for any remaining anesthetic agent within the adapter 20 or filler spout 22 to drain into the filler assembly 24 and the sump 14 before the filler valve 30 closes, closing the vaporizer filling system 12. By closing the sump valve 28 last, any remaining anesthetic agent 38 in the filler assembly 24 is provided a maximum amount of time to drain into the sump 14 before the sump 14 is closed off to fluid communication from the filler assembly 24.

However, it should be noted that in alternative embodiments, based upon practice or design considerations, the order in which the sump valve 28, the filler valve 30, and the bottle valve 58 are opened may be modified or reordered to address these other considerations.

In an embodiment, such as depicted in FIG. 2B, the adapter 20 is inserted into the filler spout 22 when the anesthetic bottle 16 is angled in an upwardly direction. This further provides the benefit of maintaining the anesthetic bottle 16 in a generally upright orientation, further decreasing any likelihood of a leak of the liquid anesthetic agent 38 while the adapter 20 engages the filler spout 22. Then, the bottle 16 is rotated about the pivot point 26 such as to place the anesthetic bottle 16 in a generally upside down orientation, or depicted in FIG. 2C. This orientation further promotes the communication of the liquid anesthetic agent 38 from the anesthetic bottle 16 into the sump 14. In an embodiment, the angle through which the anesthetic bottle 16 is rotated is 45°. However, it is to be understood that the specific angle of rotation of the anesthetic bottle 16 may be more or less than 45°, including up to or exceeding an angle of rotation of 120°.

Figure 3A:
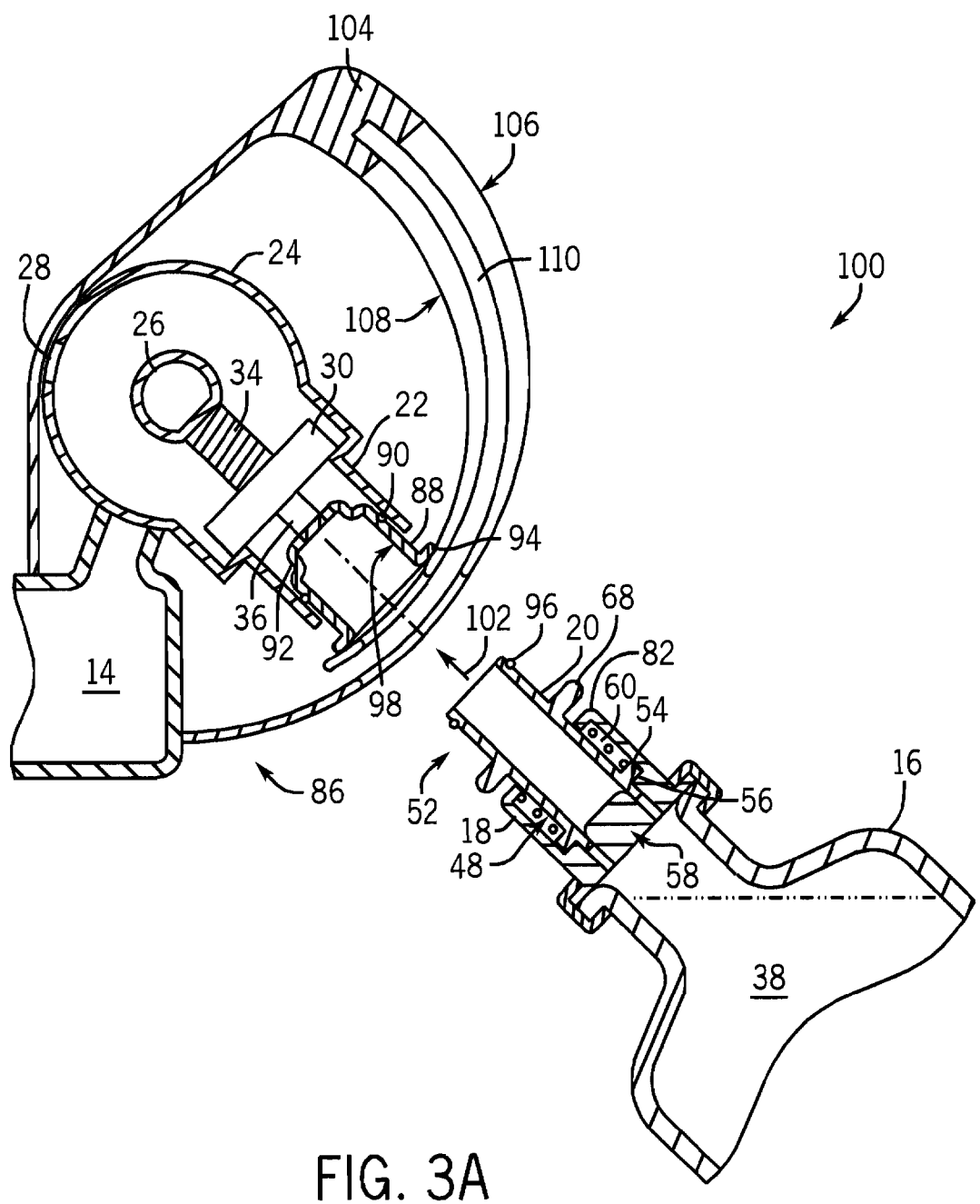
FIGS. 3A-C depicts an embodiment of a system for the delivery of a liquid anesthetic agent that includes a rail with two cam surfaces.
Figure 3B:
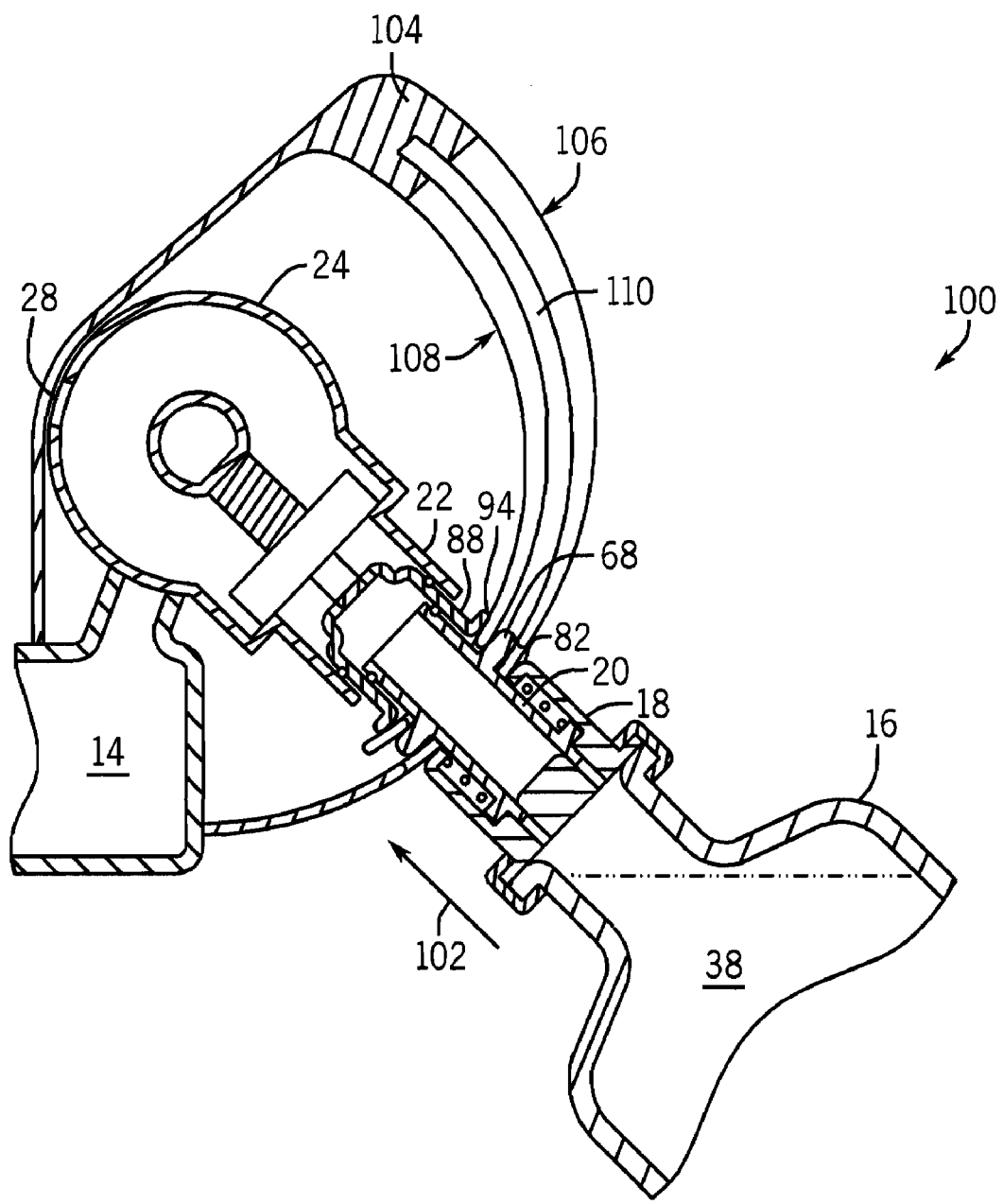
Figure 3C:
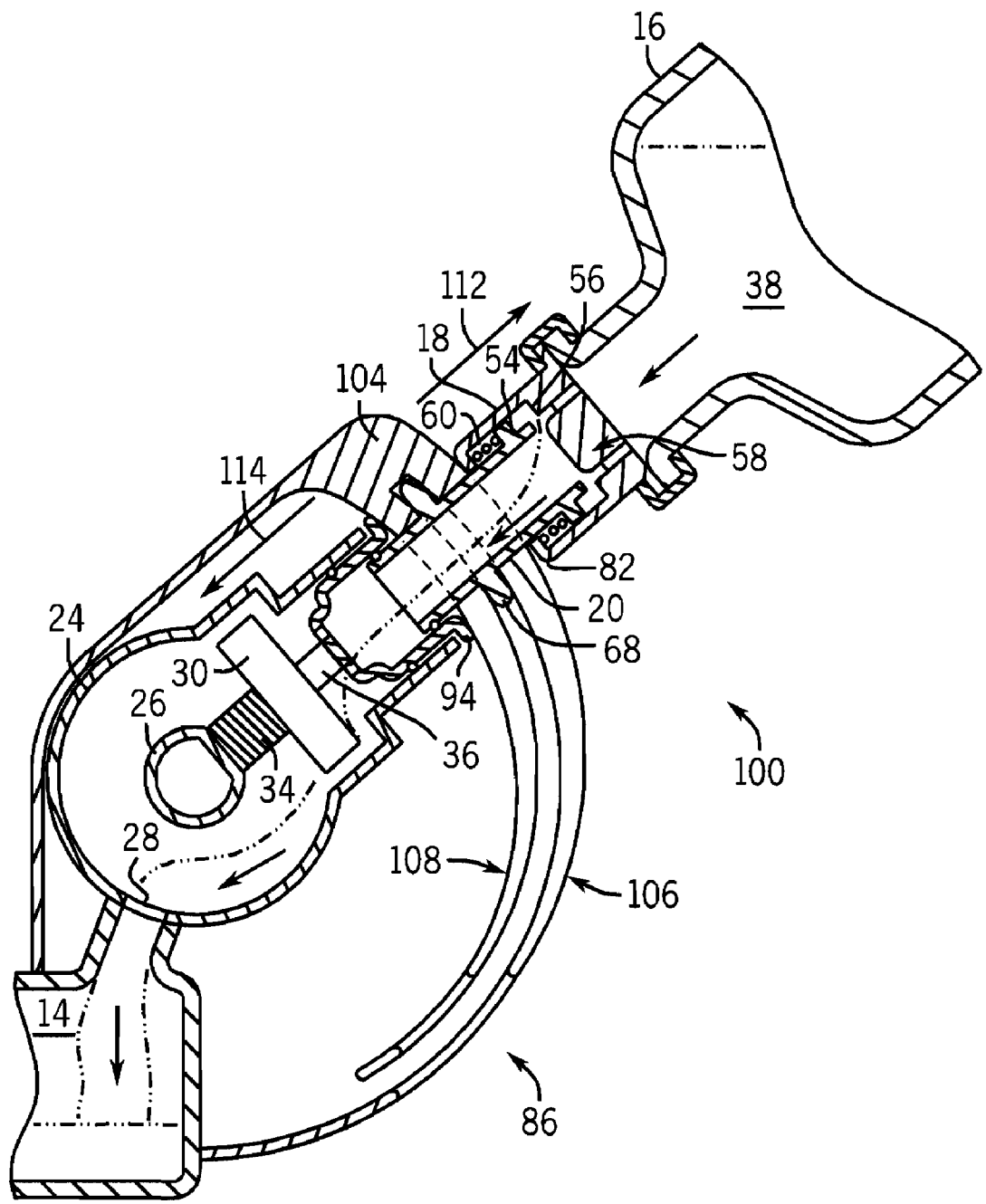

FIGS. 3A-C depict a further embodiment 100 of the system for the delivery of a liquid anesthetic agent to an anesthetic vaporizer. As noted previously, like components between the figures are numbered the same such as to maintain consistency between the embodiments.

The system 100 includes a vaporizer filling system 86 that includes the sump 14, the filler assembly 24, and the filler spout 22. The vaporizer filling system 86 further includes an intermediate connection 88 that is disposed radially interior to the filler spout 22. The intermediate connection 88 is also coaxial to the filler spout 22. The filler spout 22 includes an annular ring 90 that forms a fluid impervious seal between the filler spout 22 and the intermediate connection 88. Alternatively, the filler spout 22 and/or the intermediate connection 88 may comprise a sealing surface on the portions of the filler spout 22 and the intermediate connection 88 that engage each other. This sealing surface of the filler spout and/or the intermediate connection 88 may further create a fluid impervious seal when the intermediate connection 88 engages the filler spout 22.

The intermediate connection 88 further includes a projection 92 that engages the projection 36 of the filler valve 30. The projection 92 of the intermediate connection 88 engages the projection 36 of the filler valve 30 when the filler valve 30 is in the sealing position, such that fluid communication between the filler spout 22 and the filler assembly 24 is prevented. However, it should be noted that in alternative embodiments, the intermediate connection 88 need not engage the filler assembly 30 when the filler valve 30 is in the sealing position.

The intermediate connection 88 further includes a flange 94 that projects radially outward from the intermediate connection 88.

The adapter 20 includes a rib 68 that extends radially outward from the adapter 20. The adapter 20 further includes a bottle end 48 that forms a bottle valve 58 with the bottle cap 18. The bottle valve 58 includes a sealing surface 54 of the bottle end 48 of the adapter 20 which engages a sealing seat 56 of the bottle cap 18. A spring 60 that engages the adapter 20 and the bottle cap 18 biases the bottle valve 58 in the closed position such that fluid communication between the anesthetic bottle 16 and the adapter 20 is prevented.

The adapter 20 further includes a vaporizer end 52. The vaporizer end 52 includes an annular ring 96, or other sealing surface, that engages radially interior to the intermediate connection 88. Interior surface 98 of the intermediate connection 88 may be further include a sealing surface, such as to promote engagement between the interior surface 98 of the intermediate connection 88 and the annular ring 96 of the adapter 20. The adapter 20 is moved in the direction of arrow 102 such as to engage the intermediate connection 88. Thus, when the adapter 20 is engaged with the intermediate connection 88, the adapter 20 is coupled with the filler spout 22 through the intermediate connection 88 such that fluid communication between the adapter 20 and the filler spout 22 is established while fluid communication between the adapter 20, the intermediate connection 88, the filler spout 22, and the ambient atmosphere is prevented.

The vaporizer filling system 86 further includes a rail 104. The rail 104 includes an outer cam surface 106 and inner cam surface 108. The outer cam surface 106 defines a camming surface that diverges in a direction radially outward from the pivot point 26. The inner cam surface 108 defines a cam surface that diverges in a direction radially inward toward the pivot point 26. The rail 104 further includes an interior void 110 that is intermediate to both the outer cam surface 106 and the inner cam surface 108. The interior void 110 extends in a circumferential path equidistant from the pivot point 26. The flange 94 of the intermediate connection 88 contacts the inner cam surface 108 of the rail 104. The adapter 20 extends past the rail 104 such that the rib 68 of the adapter 20 is aligned in the inner void 110 of the rail 104. The top surface 82 of the bottle cap 18 contacts the outer cam surface 106.

In an alternative embodiment, the intermediate connection 88 is a component of the adapter 20. Therefore, the intermediate connection 88 is coupled with the adapter 20 such that the intermediate connection 88 is inserted radially interior and coaxial with the filler spout 22 with the adapter 20, rather than being a portion of the vaporizer filling system 86 and connected to the filler spout 22. In that embodiment, the intermediate connection 88 and the adapter 20 are inserted into the filler spout 22 until the flange 94 of the intermediate connection 88 is in alignment with the inner cam surface 108 of the rail 104.

Now referring to FIG. 3C, as the filler assembly 24, filler spout 22, intermediate connection 88, adapter 20, and anesthetic bottle 16 are rotated about the pivot point 26, the adapter 20, the intermediate connection 88, and the bottle cap 18 are directed in their rotational position by the rail 104. The rib 68 of the adapter 20 moves along the interior void 110. The interior void 110 is equidistant along an arc from the pivot point 26. Therefore, the rib 64 within the interior void 110 maintains the adapter 20 at the same radial distance from the pivot point 26 as the adapter 20 is moved along the rail 104. The top surface 82 of the bottle cap 18 contacts the outer cam surface 108, and therefore, as the bottle cap 18 is rotated about the pivot point along the rail 104, the bottle cap 18, and the anesthetic bottle 16 are moved in the direction of arrow 112 along a radial path that diverges outwardly from the pivot point 26. The outer cam surface 108 applies an expansive force against the top surface 82 in the direction of arrow 112. This expansive force between the rib 68 and the bottle cap 18 overcomes the biasing force of spring 60, which maintains the bottle valve 58 in the sealing position and therefore separates the sealing surface 54 of the adapter 20 from the sealing seat 56 of the bottle cap 18. This moves the bottle valve 58 into the open position, thereby opening fluid communication between the anesthetic bottle 16 and the adapter 20.

The flange 94 of the intermediate connection 88 contacts the inner cam surface 108 of the rail 104. As the intermediate connection 88 is rotated about the pivot point 26, the inner cam surface 108 applies an expansive force in the direction of arrow 114 between the rib 68 and the flange 94. The expansive force in the direction of arrow 114 separates the flange 94 of the intermediate connection 88 from the rib 68 of the adapter 20. This forces the intermediate connection 88 further into the filler spout 22 in the direction of arrow 114. The projection 92 of the intermediate connection 88 engages the projection 36 of the filler valve 30. The force of the intermediate connection 88 against the filler valve 30 overcomes the biasing force of the spring 34 that maintains the filler valve 30 in the sealing position. This moves the filler valve 30 from the sealing position into the open position and opens fluid communication between the filler spout 22 and the filler assembly 24.

As described previously, the sump valve 28 operates as a ball valve on the filler assembly 24 such that as the filler assembly 24 rotates about the pivot point 26, the sump valve 28 moves from the sealing position into the open position. This opens fluid communication between the filler assembly 24 and the sump 14.

Therefore, in the system 100 the rotating action of the filler assembly 24, filler spout 22, intermediate connection 88, adapter 20, bottle cap 18, and anesthetic bottle 16 about the pivot point 26 moves all three of the valves that prevent fluid communication. Namely, the bottle valve 58, the filler valve 30, and the sump valve 28 are moved from the sealing positions into the open positions by the upward rotation of the filler assembly 24, filler spout 22, intermediate connection 88, adapter 20, bottle cap 18, and anesthetic bottle 16. As noted previously, the sump valve 28, the filler valve 30, and the bottle valve 58 may be coordinated to open at different positions of rotation about the pivot point 26 such as to coordinate the opening and closing sequence of these valves. This movement and control, therefore, only permits the communication of the liquid anesthetic agent 38 from the anesthetic bottle 16 to the sump 14 of the vaporizer filling system 86 once the anesthetic bottle 16 has been moved up into a filling position.

Figure 4A:
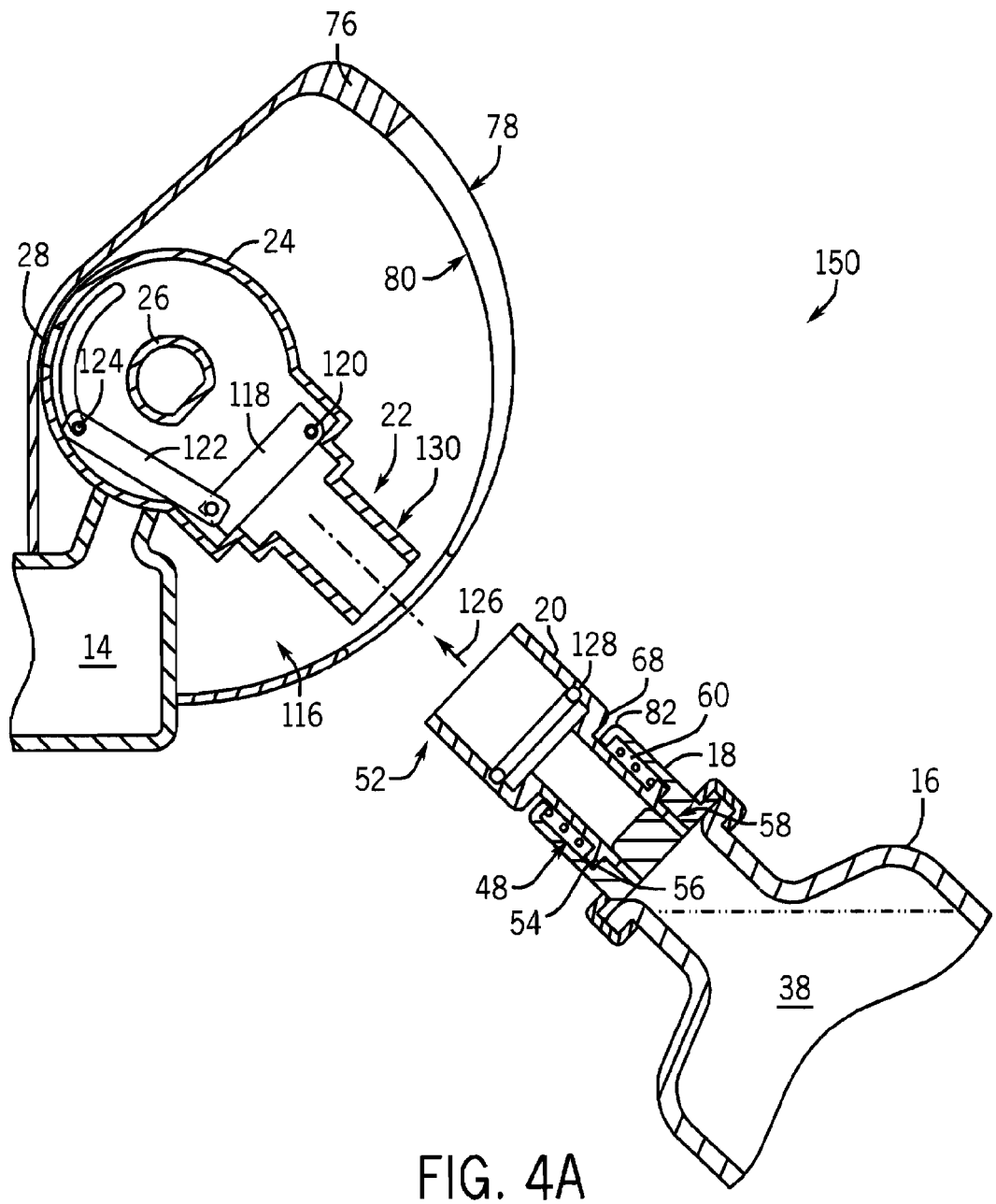
FIGS. 4A-C depicts an embodiment of a system for the delivery of a liquid anesthetic agent that includes a filler valve actionable by a linkage.
Figure 4B:
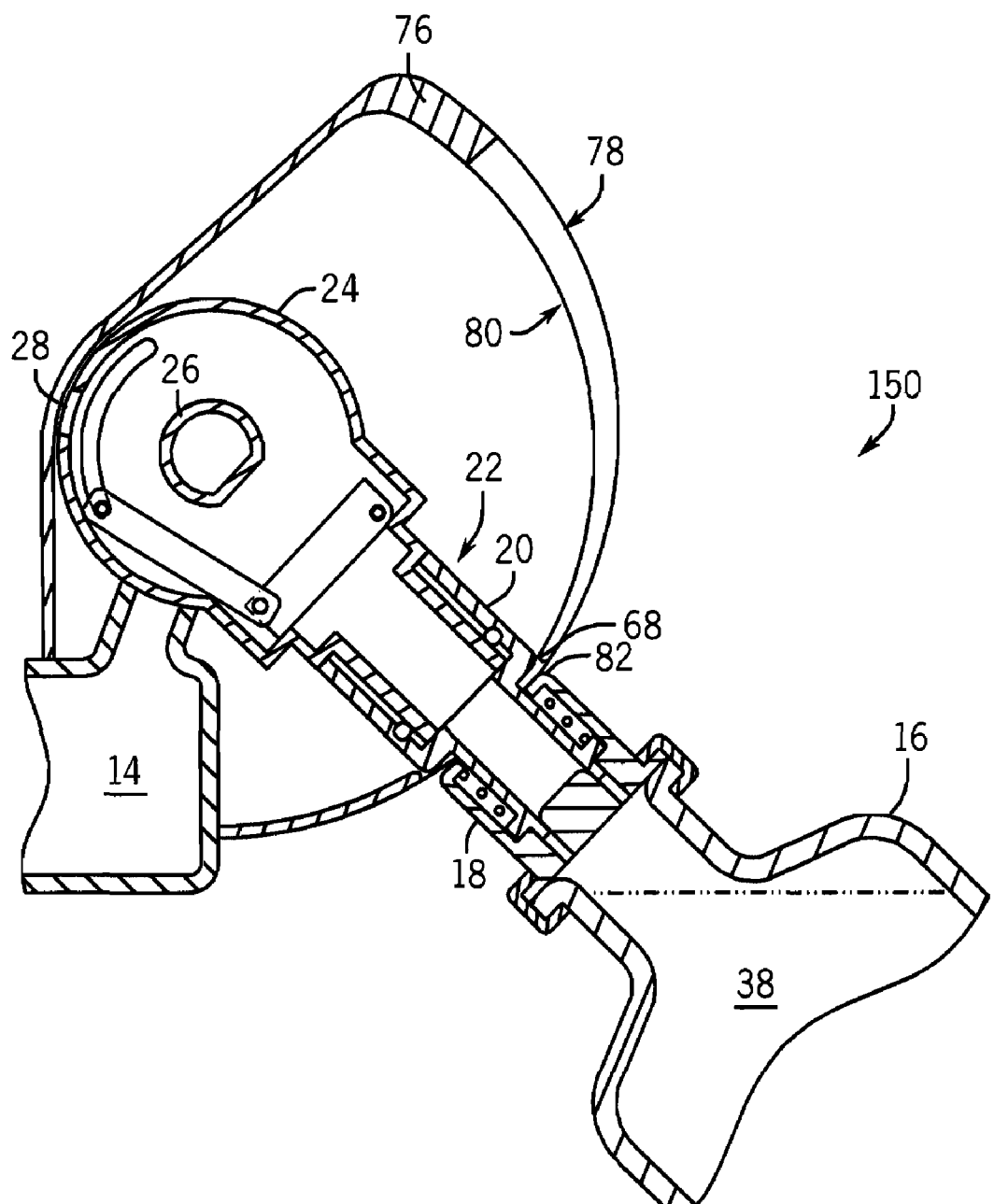
Figure 4C:
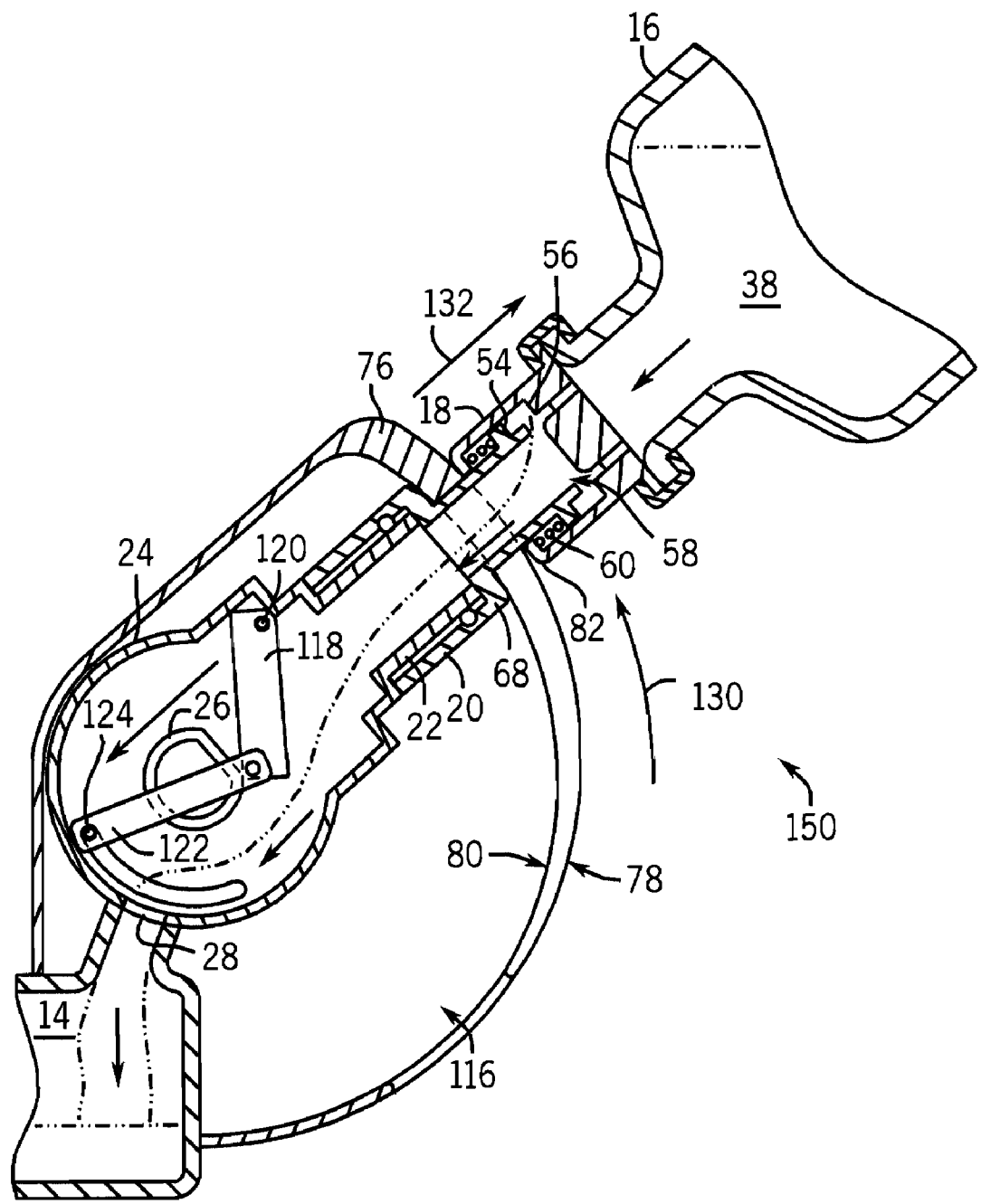

FIGS. 4A-C depict an embodiment 150 of the system for delivery of a liquid anesthetic agent to an anesthetic vaporizer. It should be noted that in the figures, like numerals are used to reference similar components common among the embodiments.

Referring to FIG. 4A, this embodiment of the system 150 includes a vaporizer filling system 116 with a sump 14, a filler assembly 24, and a filler spout 22. Fluid communication between the filler assembly 24 and the sump 14 is controlled by a sump valve 28, which may be arranged as a ball-type valve that moves from a sealed position that prevents fluid communication between the filler assembly 24 and the sump 14 and an open position that allows fluid communication between the filler assembly 24 and the sump 14 as the filler assembly 24 is rotated about a pivot point 26.

The filler assembly 24 further includes a filler valve 118 disposed between the filler assembly 24 and the filler spout 22. The filler valve 118 is movable from a sealing position that prevents fluid communication between the filler spout 22 and the filler assembly 24 and an open position that allows fluid communication between the filler spout 22 and the filler assembly 24. The filler valve 118 is connected to the filler assembly 24 at a pivot point 120. The pivot point 120 may be a hinge or a pin about which the filler valve 118 is movable. The filler valve 118 further includes a linkage 122 that extends from the filler valve 118 and is attached to a location in the filler assembly 24. In an embodiment, the linkage 122 is connected at a pivot point 124 that is located at a position behind the pivot point 26 with respect to the filler valve 118. The pivot point 124 may similarly be a hinge or a pin such that the linkage 122 is movable about the pivot point 124.

The adapter 20 includes a vaporizer end 52 and a bottle end 48. The bottle end 48 of the adapter 20 terminates in a sealing surface 54. The sealing surface 54 engages and mates with a sealing seat 56 of the bottle cap 18. The bottle cap 18 is connected to the anesthetic bottle 16. The sealing surface 54 and the sealing seat 56 form a bottle valve 58 that is biased in a sealing position by a spring 60.

The adapter 20 is configured to be moved in the direction of arrow 126 for engagement with the filler spout 22 of the vaporizer filling system 116. The adapter 20 includes a sealing surface 128, which in an embodiment, may be an annular ring. Alternatively, the sealing surface 128 may be a material or coating on the radially interior side of the adapter 20 such as to facilitate engagement with the filler spout 22 to form a fluid impervious seal. The filler spout 22 may also include a sealing surface 130 on a radially outward surface of the filler spout 22 such as to further facilitate the engagement of the adapter 20 and the filler spout 22 in a fluid impervious seal.

FIG. 4B depicts the engaged adapter 20 and filler spout 22. The adapter 20 engages the filler spout 22 in a radially exterior fashion. It is understood, however, that in alternative embodiments, the adapter 20 may engage the filler spout 22 in a radially interior fashion. When the adapter 20 is engaged with the filler spout 22, the rib 68 of the adapter 20 contacts, or is in alignment to contact, an interior surface 80 of the rail 76. Additionally, a top surface 82 of the bottle cap 18 contacts, or is in alignment to contact, the outer cam surface 78 of the rail 76. However, in an alternative embodiment, the rib 68 of the adapter 20 does not contact the interior surface 80, and the adapter 20 is held at a fixed radial distance from the pivot point 26 through its engagement with the filler spout 22.

FIG. 4C depicts the system 150 after the filler assembly 24, the filler spout 22, the adapter 20, and the anesthetic bottle 16 have been rotated about the pivot point 26 in the direction of arrow 130 as defined by the rail 76. The outer cam surface 78 diverges in a direction radially outward from the pivot point 26. This places an expansive force in the direction of arrow 132 between the rib 68 of the adapter 20 and the top surface 82 of the bottle cap 18.

The expansive force in the direction of arrow 132 against the bottle cap 18 overcomes the bias force of the spring 60 that maintains the bottle valve 58 in the sealing position, and therefore separates the engagement of the sealing surface 54 from the sealing seat 56. Therefore, this force opens the bottle valve 58 to allow fluid communication between the anesthetic bottle 16 and the adapter 20.

Looking now to the filler assembly 24, as the filler assembly 24 is rotated about the pivot point 26, the linkage 122 rotates about the pivot point 124. As the pivot point 124 is behind the pivot point 26, with respect to the filler valve 118, as the filler assembly 24 rotates about the pivot point 26, the distance between pivot point 120 and pivot point 124 increases, and therefore the linkage 122 pulls the filler valve 118 open from the sealing position, into the open position. This opens the filler valve 118 to allow fluid communication between the adapter 20 and filler spout 22 to the filler assembly 24.

The rotation of the filler assembly 24 about the pivot point 26 rotates the sump valve 28 from a sealing position into an open position, thereby permitting fluid communication between the filler assembly 24 and the sump 14.

Therefore, in the system 150, the adapter 20 is engaged with the filler spout 22, connecting the anesthetic bottle 16 to the vaporizer filling system 116. The rotation of the filler assembly 24, the filler spout 22, the adapter 20, and the anesthetic bottle 16 about the pivot point 26 in the direction of arrow 130 opens the bottle valve 58, the filler valve 118, and the sump valve 28 simultaneously, such as to open fluid communication between the anesthetic bottle 16 and the sump 14 all at once with the same mechanical motion of the anesthetic bottle 16 in the direction of arrow 130. Alternatively, as disclosed previously herein, the actuation of the sump valve 28, the filler valve 118, and the bottle valve 58 may be coordinated to open and close in a predetermined sequence. This predetermined actuation sequence may allow for additional control of the fluid communication of the anesthetic agent 38 into the sump 14. This may further facilitate the function of preventing leakage of anesthetic liquid or gas to the ambient atmosphere during the filling of the vaporizer with anesthetic agent.

This written description uses examples to disclose various embodiments, including the best mode, and also to enable any person skilled in the art to make and use these embodiments. The patentable scope is defined by the claims may extend to include other examples not explicitly listed that occur to those skilled in the art. Such other examples are intended to be within the scope of the claims if they have structural elements that do not differ from the literal language of the claims, or if they include equivalent elements with insubstantial differences from the literal languages of the claims.

Various alternatives and embodiments are contemplated as being with in the scope of the following claims, particularly pointing out and distinctly claiming the subject matter of the present disclosure.

We claim:

1. A system for the delivery of a liquid anesthetic agent to a sump of an anesthetic vaporizer, the system comprising:
a filler assembly rotatable about a pivot point, the filler assembly comprising a sump valve, the sump valve controlling fluid communication between the filler assembly and the sump as the filler assembly is rotated about the pivot point;
a filler spout connected in fluid communication with the filler assembly;
a bottle cap configured for connection to an anesthetic bottle containing liquid anesthetic agent, the bottle cap having a bottle end and an end opposite the bottle end;
an adapter having a bottle end and a vaporizer end, the bottle end being coaxial to the bottle cap and having a sealing surface that engages the bottle cap to form a seal against fluid communication between the anesthetic bottle and the adapter, the vaporizer end of the adapter extending away from the bottle cap, the vaporizer end of the adapter coupling with the filler spout; and
a rail coupled to the anesthetic vaporizer, the rail having a cam surface, the cam surface varying in radial distance from the pivot point, the bottle cap contacting the rail such that rotation of the bottle cap and the adapter about the pivot point causes the cam surface of the rail to push the bottle cap radially along an axis from the pivot point, disengaging the sealing surface of the adapter from the bottle cap and opening the adapter to fluid communication with the anesthetic bottle.

2. The system of claim 1 further comprising:
a filler valve disposed between the filler assembly and the filler spout, the filler valve having a sealing position preventing fluid communication between the filler spout and the filler assembly and an open position allowing fluid communication between the filler spout and the filler assembly; and
a linkage extending from the filler assembly to a filler valve, the linkage actuating the filler valve between the sealing position and the open position as the filler assembly is rotated about the pivot point.

3. The system of claim 1 wherein a radially exterior surface of the adapter engages a radially interior surface of the filler spout.

4. The system of claim 3 further comprising:
a filler valve disposed between the filler assembly and the filler spout, the filler valve operating between a sealing position preventing fluid communication therethrough and the filler assembly and an open position allowing fluid communication therethrough;
wherein the adapter engages the filler valve and coaxial movement of the adapter within the filler spout in a direction towards the pivot point actuates the filler valve to move from the sealing position to the open position.

5. The system of claim 4 further comprising a bottle valve that comprises the bottle cap and the bottle end of the adapter, the bottle valve operating between a sealing position preventing fluid communication therethrough, and an open position allowing fluid communication therethrough;
wherein the rotation of the adapter and the bottle cap about the pivot point and along the rail operates the bottle valve and the filler valve between the sealing position and the open position in a predetermined sequence.

6. The system of claim 1 wherein the cam surface of the rail is an outer cam surface and the rail further comprises an inner cam surface, the inner cam surface and the outer cam surface diverging in radial distance from the pivot point.

7. The system of claim 6 further comprising an intermediate connection disposed between the adapter and the filler spout, the intermediate connection engaging the adapter and engaging the filler spout, the intermediate connection further comprising a projection configured to engage the inner cam surface of the rail.

8. The system of claim 7 wherein the intermediate connection further engages a filler valve disposed between the filler assembly and the filler spout and a camming action between the inner cam surface and the outer projection surface, as the intermediate connector is rotated about the pivot point along the rail, actuates the filler valve from a sealing position preventing fluid communication between the filler spout and the filler assembly, to an open position, allowing fluid communication between the filler spout and the filler assembly.

9. An adapter apparatus for connection between an anesthetic bottle and an anesthetic vaporizer, the adapter comprising:
   a bottle cap configured at one end for connection to the anesthetic bottle, the bottle cap having an open interior;
   an adapter with a bottle end and a vaporizer end, the bottle end terminating in a sealing surface that couples with the bottle cap to form a seal against fluid communication, the vaporizer end extending away from the bottle cap, the vaporizer end configured to couple with the anesthetic vaporizer, the adapter further comprising a rib extending radially outward from the adapter;
   wherein a force applied to at least one of the bottle cap and the rib of the adapter increases the distance between the bottle cap and the rib and separates the sealing surface of the adapter from the bottle cap, thereby opening fluid communication between the bottle cap and the adapter.

10. The apparatus of claim 9 wherein a radially exterior surface of the vaporizer end of the adapter is configured to couple with the vaporizer.

11. The apparatus of claim 9 further comprising an intermediate connection, the intermediate connection being coaxial with the adapter, the intermediate connection configured to couple with the vaporizer, the intermediate connection further comprising a projection wherein a force applied to at least one of the intermediate connection and the rib of the adapter extends the intermediate connection coaxially away from the adapter.

12. The apparatus of claim 9 further comprising a spring disposed within the bottle cap and radially exterior to the adapter, the spring applying a force against the bottle cap and the adapter to bias the sealing surface of the adapter in engagement with the bottle cap.

13. An anesthetic vaporizer comprising:
   a sump positioned in the anesthetic vaporizer to receive and store liquid anesthetic agent;
   a filler assembly configured to rotate about a pivot point in the filler assembly, the filler assembly connected to the sump through a sump valve, the sump valve being actuated by the rotation of the filler assembly about the pivot point;
   a filler spout connected to the filler assembly and extending radially away from the pivot point of the filler assembly, the filler spout having a hollow interior for fluid communication therethrough, the filler spout being configured to establish fluid communication with an anesthetic bottle;
   a filler valve positioned between the filler assembly and the filler spout, the filler valve movable between a sealing position wherein the filler valve prevents fluid communication between the filler spout and the filler assembly and an open position wherein the filler valve allows fluid communication between the filler spout and the filler assembly; and
   a rail having a cam surface at a radially diverging distance from the pivot point of the filler assembly.

14. The anesthetic vaporizer of claim 13 wherein the filler valve is movable from the sealing position to the open position by pressure against the filler valve in the direction of the pivot point.

15. The anesthetic vaporizer of claim 14 further comprising a spring connected between the filler assembly and the filler valve, the spring biasing the filler valve in the sealing position.

16. The anesthetic vaporizer of claim 13 further comprising a linkage extending from the filler assembly to the filler valve, the linkage moving the filler valve between the sealing position and the open position as the filler assembly is rotated about the pivot point.

17. The anesthetic vaporizer of claim 13 wherein the filler spout is configured to couple with an anesthetic bottle to establish fluid communication between the anesthetic bottle and the filler spout.

18. The system of claim 13 wherein the cam surface of the rail is an inner cam surface at a distance from the pivot point that diverges radially inward.

19. The system of claim 18 further comprising an intermediate connection coaxial with and radially interior to the filler spout, and being configured to couple with an anesthetic bottle, the intermediate connection further comprising a projection configured to contact the inner cam surface of the rail.

20. The system of claim 19 wherein the intermediate connection further engages the filler valve and a camming action between the inner cam surface and the projection, as the intermediate connector is rotated about the pivot point, actuates the filler valve from the sealing position to the open position.

* * * * *